US012298325B2

(12) United States Patent
Wang et al.

(10) Patent No.: US 12,298,325 B2
(45) Date of Patent: May 13, 2025

(54) METHOD AND APPARATUS FOR DETERMINING CONTENT OF ADSORBED GAS IN DEEP SHALE, AND SERVER

(71) Applicant: China University of Petroleum-Beijing, Beijing (CN)

(72) Inventors: Jing Wang, Beijing (CN); Zhengfu Ning, Beijing (CN); Chunyu Ren, Beijing (CN); Zheng Zhou, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 657 days.

(21) Appl. No.: 17/584,291

(22) Filed: Jan. 25, 2022

(65) Prior Publication Data
US 2022/0252492 A1    Aug. 11, 2022

(30) Foreign Application Priority Data
Jan. 25, 2021    (CN) ......................... 202110096155.X

(51) Int. Cl.
G01N 7/04        (2006.01)
G01N 33/24       (2006.01)

(52) U.S. Cl.
CPC ............. G01N 7/04 (2013.01); G01N 33/241 (2013.01)

(58) Field of Classification Search
CPC ............................... G01N 7/04; G01N 33/241
See application file for complete search history.

(56) References Cited

U.S. PATENT DOCUMENTS
2011/0239732 A1    10/2011    Zhang et al.

FOREIGN PATENT DOCUMENTS
CN    104153770 A   * 11/2014
CN    104215559       12/2014
(Continued)

OTHER PUBLICATIONS

Hexin Huang "Investigation of variation in shale gas absorption capacity with burial depth: Insights from the absorption potential theory". pp. 1-11, Journal of Natural Gas Science and Engeeneering (Year: 2019).*

(Continued)

Primary Examiner — Michael J Dalbo
Assistant Examiner — Kaleria Knox
(74) Attorney, Agent, or Firm — LOZA & LOZA, LLP; Michael F. Fedrick

(57) ABSTRACT

A method and apparatus for determining content of adsorbed gas in a deep shale, and a server, wherein experimental tests are combined with molecular dynamics models. Firstly, tests are performed on a core sample of a target area at various temperatures in a first-class pressure environment with low pressure to obtain shale gas adsorption data of the core sample; next, a first shale molecule dynamics model of the core sample is established, and a fitting adjustment is performed on the first shale molecule dynamics model using the shale gas adsorption data to obtain a second shale molecule dynamics model. Further, the second shale molecular dynamics model is used to obtain, by analogue simulation, shale gas adsorption data of the core sample corresponding to the various temperatures in a second-class pressure environment with high pressure, so as to obtain an accurate and comprehensive adsorption characteristic curve in a full pressure range.

7 Claims, 8 Drawing Sheets

(56) References Cited

FOREIGN PATENT DOCUMENTS

| CN | 104215559 | A | * | 12/2014 | | |
|---|---|---|---|---|---|---|
| CN | 104239602 | A | * | 12/2014 | | |
| CN | 106153495 | | | 11/2016 | | |
| CN | 106153495 | A | * | 11/2016 | ............... | G01N 7/04 |
| CN | 106290057 | | | 1/2017 | | |
| CN | 108106964 | | | 6/2018 | | |
| CN | 108446526 | | | 8/2018 | | |
| CN | 109214026 | A | * | 1/2019 | | |
| CN | 109799164 | | | 5/2019 | | |
| CN | 110672813 | | | 1/2020 | | |
| CN | 110849766 | | | 2/2020 | | |
| CN | 112014287 | | | 12/2020 | | |
| CN | 112162000 | | | 1/2021 | | |

OTHER PUBLICATIONS

Changan Shan et al., Influence of chemical properties on CH4 absorption capacity of anthracite derived from southern Sichuan Basin, China, pp. 387-401; Marine and Petroleun Geology (Year: 2018).*

China Petroleum Natural Gas Industry Standard, "The method of separation and examination of heavy minerals for sedimentary rock," issued by the National Energy Administration of China, Document No. SY/T 6336-2019 (2019).

Cao, Jinrong, et al. "Molecular Simulation of Methane Adsorption Behavior in Kerogen Nanopores for Shale Gas Resource Assessment." International Petroleum Technology Conference. International Petroleum Technology Conference, held in Beijing, China, Mar. 26-28, 2019, 19 pages.

R.B.Anderson et al., "Equilibrium Sorption Studies of Methane on Pittsburgh Seam and Pocahontas No. 3 Seam Coal," Coal Science, 1966, 55(24): 386-399, 14 pages.

National Standards of the People's Republic of China, "Experimental method of high-pressure adsorption isothermal to coal-capacity method," Document No. GB/T19560-2004 (2004).

Baohe Wei, et al., "Quantitative analysis method of rock mineral energy spectrum, Oil and Gas Industry Standards of the People's Republic of China," China National Petroleum Corporation, incorporated into National Standards of the People's Republic of China, Document No. SY/T6189-201 (1996).

Brunauer S, Emmett P, Teller E, "Adsorption of gases in multimolecular layers," Journal of the American Chemical Society, 1938, 602:309-319.

First Office Action and Search Report issued on Oct. 8, 2021 for counterpart Chinese Patent Application No. 202110096155.X, 8 pages.

Liehui, Zhang, Shan Baochao, Zhao Yulong, and Guo Zhaoli, "Review of Micro Seepage Mechanisms in Shale Gas Reservoirs," International Journal of Heat and Mass Transfer, 139: 144-179 (2019).

Huang, Hexin, Li, Rongxi, Jiang, Zhenxue, Li, Jian, and Chen, Lei, "Investigation of Variation in Shale Gas Adsorption Capacity with Burial Depth: Insights from the Adsorption Potential Theory," Journal of Natural Gas Science and Engineering, Jan. 2020, vol. 73:103043 (2020), 11 pages.

Ju, Yang, Jian He, Elliot Chang, and Liange Zheng, "Quantification of CH4 Adsorption Capacity in Kerogen-rich Reservoir Shales: An Experimental Investigation and Molecular Dynamic Simulation", Energy, 170:411-422 (2019).

Polanyi M, "The potential theory of adsorption," Science, 1963, 141:1010-1013.

Supplementary Search Report issued on Jan. 17, 2022 for counterpart Chinese Patent Application No. 202110096155.X, Jan. 25, 2021, 6 pages.

\* cited by examiner

METHOD AND APPARATUS FOR DETERMINING CONTENT OF ADSORBED GAS IN DEEP SHALE, AND SERVER

CROSS-REFERENCE TO RELATED APPLICATIONS

This application claims the benefit of priority under 35 U.S.C. § 119 from Chinese Patent Application No. 202110096155.X, filed on Jan. 25, 2021 and entitled "METHOD AND APPARATUS FOR DETERMINING CONTENT OF ADSORBED GAS IN DEEP SHALE, AND SERVER." The disclosure of the foregoing application is incorporated herein by reference in its entirety.

TECHNICAL FIELD

The present disclosure relates to a technical field of oil reservoir exploitation, and particularly to a method and apparatus for determining content of adsorbed gas in a deep shale, and a server.

BACKGROUND

Shale gas is usually stored in free and adsorbed states in dark mud shale or high carbon mud shale, wherein the adsorbed state (i.e., the adsorbed gas) is the main occurrence form of the shale gas. The statistical results show that the adsorbed gas usually accounts for about 20% to 85% of the total gas volume. Thus, the determination of adsorption data such as adsorption and desorption characteristics of the shale gas is greatly significant for analyzing and determining occurrence characteristics of the shale gas, evaluating the quantity of the shale gas resource, predicting and optimizing the production capacity of the shale gas, etc.

Most deep shale gas reservoirs are ultra-high pressure and high-temperature gas reservoirs. For example, the maximum pressure may be up to 100 MPa. However, the conventional experimental test conditions cannot provide the above high-pressure for adsorption temperature tests. Therefore, it is difficult to obtain accurate deep shale gas adsorption data in the high-pressure environment through experimental tests based on prior arts. As a result, it is impossible to obtain accurate and comprehensive shale gas adsorption data of a full pressure range.

At present, there is no effective solution for the above problems.

SUMMARY

The present disclosure provides a method and apparatus for determining content of adsorbed gas in a deep shale, and a server, so as to obtain accurate shale gas adsorption data in a second-class pressure environment with high pressure, and integrate the above adsorption data with that in a first-class pressure environment with low pressure to obtain an accurate and comprehensive adsorption characteristic curve in a full pressure range.

The present disclosure provides a method for determining content of adsorbed gas in a deep shale, comprising:
obtaining a core sample of a target area;
performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold;
establishing a first shale molecular dynamics model for the core sample;
adjusting the first shale molecular dynamics model based on the shale gas adsorption data of the core sample corresponding to the various temperatures in the first-class pressure environment to obtain a second shale molecular dynamics model;
obtaining, by analog simulation using the second shale molecular dynamics model, shale gas adsorption data of the core sample corresponding to the various temperatures in a second-class pressure environment; and
determining an adsorption characteristic curve of the core sample in a full pressure range, based on the shale gas adsorption data of the core sample corresponding to the various temperatures in the first-class and second-class pressure environments.

In one embodiment, performing tests on the core sample at the various temperatures in the first-class pressure environment to obtain shale gas adsorption data of the core sample corresponding to the various temperatures in the first-class pressure environment comprises:
performing isothermal adsorption tests on the core sample at the various temperatures in the first-class pressure environment to obtain excess adsorption capacities of shale gas corresponding to the various temperatures; and
calculating, based on the excess adsorption capacities of shale gas corresponding to the various temperatures, absolute adsorption capacities of shale gas corresponding to the various temperatures, as the shale gas adsorption data of the core sample corresponding to the various temperatures in the first-class pressure environment.

In one embodiment, establishing the first shale molecular dynamics model for the core sample comprises:
performing a total rock diffraction mineral measurement on the core sample to determine contents of various mineral in the core sample; and
establishing the first shale molecular dynamics model for the core sample based on composite structure of clay minerals and organic matters and the contents of the various minerals in the core sample.

In one embodiment, adjusting the first shale molecular dynamics model based on the shale gas adsorption data of the core sample corresponding to the various temperatures in the first-class pressure environment to obtain the second shale molecular dynamics model comprises:
establishing an adsorption characteristic curve of the core sample in a first-class pressure range, based on the shale gas adsorption data of the core sample corresponding to the various temperatures in the first-class pressure environment; and
adjusting the contents of the minerals and model parameters involved in the first shale molecular dynamics model by fitting the adsorption characteristic curve of the core sample in the first-class pressure range, to obtain the second shale molecular dynamics model.

In one embodiment, obtaining, by analog simulation using the second shale molecular dynamics model, shale gas adsorption data of the core sample corresponding to the various temperatures in the second-class pressure environment comprises:
selecting a plurality of pressure environment variables matched with pressures of the target area form the second-class pressure environment, wherein the second-class pressure environment comprises a plurality of pressures with pressure values greater than a preset pressure threshold; and performing, by the second shale molecular dynamics model, isothermal adsorption molecular simulations at the various temperatures respectively based on the pressure environment variables, to calculate the shale gas adsorption data of the core sample corresponding to the various temperatures in the second-class pressure environment.

In one embodiment, after determining the adsorption characteristic curve of the core sample in the full pressure range, the method further comprises:

performing a shale gas development in the target area based on the adsorption characteristic curve of the core sample in the full pressure range.

In one embodiment, the method further comprises:

determining adsorption characteristic curves of a plurality of groups of core samples in the full pressure range, wherein mineral components of core samples in different groups among the plurality of groups of core samples are different from each other;

performing a fitting regression using a multi-factor formula based on the adsorption characteristic curves of the plurality of groups of core samples in the full pressure range to obtain a deep shale gas adsorption capacity multi-factor prediction model, wherein the deep shale gas adsorption capacity multi-factor prediction model is capable of predicting shale gas adsorption data of the core samples with different mineral components corresponding to different temperatures in different pressure environments.

The present disclosure further provides an apparatus for determining content of adsorbed gas in a deep shale, comprising:

an obtaining module configured to obtain a core sample of a target area;

a testing module configured to perform tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold;

an establishing module configured to establish a first shale molecular dynamics model for the core sample;

an adjusting module configured to adjust the first shale molecular dynamics model based on the shale gas adsorption data of the core sample corresponding to the various temperatures in the first-class pressure environment to obtain a second shale molecular dynamics model;

a simulating module configured to obtain, by analog simulation using the second shale molecular dynamics model, shale gas adsorption data of the core sample corresponding to the various temperatures in a second-class pressure environment; and a determining module configured to determine an adsorption characteristic curve of the core sample in a full pressure range, based on the shale gas adsorption data of the core sample corresponding to the various temperatures in the first-class and second-class pressure environments.

The present disclosure further provides a server, comprising a processor and a memory configured to store instructions executable by the processor, and the processor is configured to execute the instructions to implement: obtaining a core sample of a target area; performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold; establishing a first shale molecular dynamics model for the core sample; adjusting the first shale molecular dynamics model based on the shale gas adsorption data of the core sample corresponding to the various temperatures in the first-class pressure environment to obtain a second shale molecular dynamics model; obtaining, by analog simulation using the second shale molecular dynamics model, shale gas adsorption data of the core sample corresponding to the various temperatures in a second-class pressure environment; and determining an adsorption characteristic curve of the core sample in a full pressure range, based on the shale gas adsorption data of the core sample corresponding to the various temperatures in the first-class and second-class pressure environments.

The present disclosure further provides a computer-readable storage medium storing computer instructions, and when being executed by the processor, the instructions implement: obtaining a core sample of a target area; performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold; establishing a first shale molecular dynamics model for the core sample; adjusting the first shale molecular dynamics model based on the shale gas adsorption data of the core sample corresponding to the various temperatures in the first-class pressure environment to obtain a second shale molecular dynamics model; obtaining, by analog simulation using the second shale molecular dynamics model, shale gas adsorption data of the core sample corresponding to the various temperatures in a second-class pressure environment; and determining an adsorption characteristic curve of the core sample in a full pressure range, based on the shale gas adsorption data of the core sample corresponding to the various temperatures in the first-class and second-class pressure environments.

According to the method and apparatus for determining content of adsorbed gas in a deep shale, and a server provided by the embodiments of the present disclosure, experimental tests are combined with molecular dynamics models. On one hand, firstly, experimental tests are performed on a core sample in a target area at various temperatures in a first-class pressure environment with low pressure, so as to obtain shale gas adsorption data of the core sample corresponding to the various temperatures in the first-class pressure environment. On the other hand, a first shale molecular dynamics model for the core sample is established, and a fitting adjustment is performed on the first shale molecular dynamics model using the previously obtained shale gas adsorption data of the core sample corresponding to the various temperatures in the first-class pressure environment, so as to obtain a second shale molecular dynamics model with higher accuracy and better effect. Further, the second shale molecular dynamics model may be used to obtain, by performing an analog simulation, shale gas adsorption data of the core sample corresponding to the various temperatures in a second-class pressure environment where the pressure is high and the experimental tests are difficult to carry out. Therefore, accurate adsorption data in the second-class pressure environment with high pressure can be obtained by combining the experimental tests with the molecular dynamics models. Further, an accurate and comprehensive adsorption characteristic curve in a full pressure range can be obtained by integrating the adsorption data in the first-class and second-class pressure environments. The present disclosure solves the technical problem that it is impossible to obtain accurate and comprehensive adsorption characteristics in a full pressure range due to the lack of adsorption data in the second-class pressure environment with high pressure, wherein the adsorption data is difficult to obtain through the conventional method.

BRIEF DESCRIPTION OF DRAWINGS

For clearer illustration of the embodiments in the present disclosure, a brief description of the drawings for the embodiments will be given below. The drawings described below involve only some embodiments of the present disclosure. For those of ordinary skill in the art, other drawings can be derived from these drawings without any inventive efforts.

DESCRIPTION OF EMBODIMENTS

For a better understanding of the technical features of the present disclosure, a clear and complete description of the embodiments of the present disclosure will be set forth with reference to the drawings. Obviously, the described embodiments are only a part, rather than all, of the embodiments of the present disclosure. All other embodiments derived by persons skilled in the art from the embodiments of the present disclosure without making inventive efforts shall fall within the protection scope of the present disclosure.

Most deep shale gas reservoirs are ultra-high pressure and high-temperature gas reservoirs. For example, the pressure may be up to 100 MPa. However, limited by the existing experimental test conditions, it is often difficult to perform tests at temperatures in the above high-pressure environment by simulation. As a result, it is difficult to obtain accurate shale gas adsorption data in the high-pressure environment based on the prior arts, and it is impossible to obtain accurate and comprehensive shale gas adsorption data of a full pressure range.

Concerning the root causes of the above problems, the present disclosure considers combining laboratory-based experimental tests with molecular dynamics models. Firstly, by using existing experimental test conditions, experimental tests are performed on a core sample of a target area at various temperatures in a first-class pressure environment with low pressure, to obtain shale gas adsorption data of the core sample corresponding to the various temperatures in the first-class pressure environment. Meanwhile, it is possible to establish a first shale molecular dynamics model for the core sample based on mineral components thereof, and obtain a second shale molecule dynamics model with higher accuracy and better effect by performing a fitting adjustment of the first shale molecular dynamics model using the shale gas adsorption data corresponding to the various temperatures in the first-class pressure environment obtained previously. Further, it is possible to calculate, by analog simulation using the second shale molecular dynamics model, shale gas adsorption data of the core sample corresponding to the various temperatures in a second-class pressure environment where the pressure is high and experimental tests are difficult to carry out. Then the adsorption data in the first-class pressure environment and the adsorption data in the second-class pressure environment can be integrated to obtain an accurate and comprehensive adsorption characteristic curve in a full pressure range for the core sample.

Figure 1:
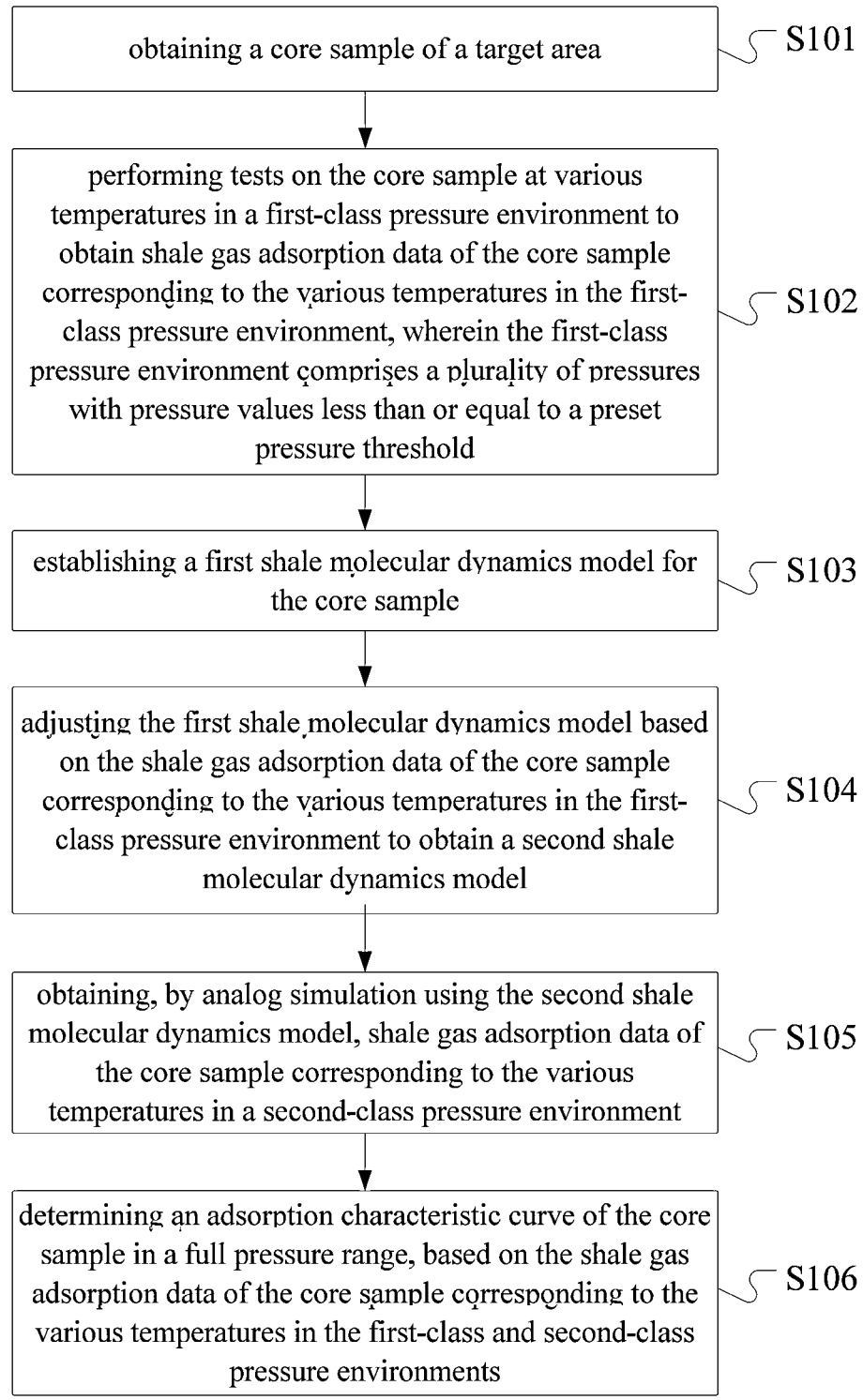
FIG. 1 is a schematic flow diagram of a method for determining content of adsorbed gas in a deep shale provided by an embodiment of the present disclosure.

Based on the above ideas, referring to FIG. 1, an embodiment of the present disclosure provides a method for determining content of adsorbed gas in a deep shale. During implementation, the method may comprise the following content.

S101: obtaining a core sample of a target area.

In this embodiment, the target area specifically may comprise an area to be explored or developed for shale gas. A core sample may be collected from the target area as the core sample of the target area.

S102: performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold.

In one embodiment, the first-class pressure environment specifically may comprise a plurality of pressures with pressure values less than or equal to the preset pressure threshold. The preset pressure threshold may be determined based on pressure values achievable by existing experimental test conditions. The first-class pressure environment may be understood as a pressure set composed of a plurality of pressures with pressure values less than or equal to the preset pressure threshold.

Specifically, for example, the preset pressure threshold may be set to 20 MPa. Of course, this pressure threshold is just a schematic illustration. During implementation, the preset pressure threshold can be flexibly set to an appropriate pressure value according to actual experimental test conditions.

In one embodiment, during implementation, the core sample may be divided into a plurality of test samples according to existing experimental test conditions; an experimental test (e.g., an isothermal adsorption test) is performed on the plurality of test samples respectively under a combined state of a certain pressure in the first-class pressure environment and a certain temperature, and the corresponding data is collected; and adsorption data corresponding to the combined state of the pressure and the temperature is determined based on the collected data, thereby obtaining shale gas adsorption data corresponding to the various temperatures in the first-class pressure environment (i.e., shale adsorbed gas contents corresponding to the various temperatures in the first-class pressure environment).

In one embodiment, performing tests on the core sample at the various temperatures in the first-class pressure environment to obtain the shale gas adsorption data of the core sample corresponding to the various temperatures in the first-class pressure environment may comprise:

S1: performing isothermal adsorption tests on the core sample at the various temperatures in the first-class pressure environment to obtain excess adsorption capacities of shale gas corresponding to the various temperatures;

S2: calculating, based on a density of adsorbed phase of shale gas and the excess adsorption capacities of shale gas corresponding to the various temperatures, absolute adsorption capacities of shale gas corresponding to the various temperatures, as the shale gas adsorption data of the core sample corresponding to the various temperatures in the first-class pressure environment.

In one embodiment, the experimental tests may be performed with a shale gas isothermal adsorption experimental apparatus according to experimental rules specified in national standard GB/T19560-2004 'Experimental Method of High-Pressure Adsorption Isothermal to Coal-Capacity Method' of China.

A reference kettle and a sample kettle used in the experimental tests are both made of stainless steel, and each equipped with a pressure sensor to measure gas pressure therein. The maximum bearable pressure of the pressure sensor may be 35 MPa with an accuracy of 0.03%.

In this embodiment, considering the specific situation of the target area, and considering that the shale adsorption is single-component adsorption of methane, the experimental temperature can be set to 40-80° C., and the pressure can be set to 0-20 MPa. The specific process of the experimental test may comprise the following steps.

S1: performing a preprocess on a core sample to obtain a preprocessed core sample.

S2: checking tightness of experimental devices and apparatuses.

S3: calibrating volumes of the reference kettle and the sample kettle.

S4: calibrating volumes of a middle area and a free area.

S5: after completing the above preparation steps and confirming that the tightness of the experimental devices and apparatuses is qualified, a shale gas single-component isothermal adsorption experiment (or test) is specifically performed as follows.

In a specific experimental test, a corresponding temperature may be set and the whole experimental system may be evacuated, and then high-pressure gas with a corresponding pressure may be injected into the reference kettle until the pressure is stable. Next, the gas in the reference kettle is gradually transferred to the sample kettle by opening and closing corresponding pneumatic valves. It should be noted that the reference kettle and the sample kettle remain disconnected to each other during the whole experiment. Finally, an excess adsorption capacity of methane is obtained based on the law of conservation of mass, and the excess adsorption capacity is taken as an excess adsorption capacity of shale gas corresponding to the temperature in the first-class pressure environment.

S6: replacing the core sample with another core sample and repeating step S5 to perform the experimental test again, until all core samples are tested.

S7: converting the excess adsorption capacities obtained in the experimental test into absolute adsorption capacities, the absolute adsorption capacities being taken as the shale gas adsorption data of the core samples corresponding to the various temperatures in the first-class pressure environment.

In one embodiment, during the specific implementation, the absolute adsorption capacities of shale gas corresponding to the various temperatures, being taken as the shale gas adsorption data of the core sample corresponding to the various temperatures in the first-class pressure environment, may be calculated based on the density of adsorbed phase of shale gas and the excess adsorption capacities of shale gas corresponding to the various temperatures.

Specifically, the density of adsorbed phase of shale gas of the core sample under a high pressure may firstly be studied in an optimized method, without making any assumption on the state of the adsorbed phase. Further, the density of adsorbed phase may be taken as an unknown number to participate in fitting, and then the fitting result is compared with a reference density of adsorbed phase to calculate an accurate absolute adsorption capacity.

During implementation, the following formula (1) may be determined according to a Gibbs excess adsorption isotherm to represent the relationship between the excess adsorption capacity and the absolute adsorption capacity:

$$n_{exc}^{Gibbs} = n_{ads}^{Abs}\left(1 - \frac{\rho_{gas}}{\rho_{ads}}\right) \quad (1)$$

wherein $n_{exec}^{Gibbs}$ denotes a Gibbs excess adsorption capacity, $n_{ads}^{Abs}$ denotes a Gibbs absolute adsorption capacity, $\rho_{gas}$ denotes a free gas density, and $\rho_{abs}$ denotes an adsorbed gas density.

Meanwhile, a Langmuir equation shown in formula (2) is further introduced:

$$n_{abs} = n_L \frac{bP}{1+bP} \quad (2)$$

wherein $n_{abs}$ denotes an absolute adsorption capacity, $n_L$ denotes a Langmuir adsorption capacity, b denotes an adsorption coefficient, and P denotes a gas phase pressure.

Further, formulas (1) and (2) are combined to obtain a corrected relational expression between the excess adsorption capacity and the absolute adsorption capacity as shown in formula (3), which has higher accuracy and better effect.

$$n_{exc} = n_L \frac{bP}{1+bP}\left(1 - \frac{\rho_{gas}}{\rho_{ads}}\right) \quad (3)$$

wherein $n_{exec}$ denotes an excess adsorption capacity.

Next, the excess adsorption capacity obtained in the experimental test and other parameters may be substituted into the corrected relational expression between the excess adsorption capacity and the absolute adsorption capacity, thereby obtaining an accurate absolute adsorption capacity of shale gas by fitting.

Specifically, when the corrected relational expression between the excess adsorption capacity and the absolute adsorption capacity is used, the density of adsorbed phase may be treated as an atmospheric boiling point density, i.e., $\rho_{ads}=0.421$ g/cm$^3$ may be substituted into the corrected relational expression (3) for calculating and fitting, so as to obtain an accurate absolute adsorption capacity.

S8: changing the set temperature, and repeating steps S5, S6 and S7 to perform the isothermal adsorption experiment to obtain the absolute adsorption capacities at different temperatures and different pressures in the first-class pressure environment.

According to the above embodiments, the existing experimental test conditions can be fully and effectively utilized to obtain accurate shale gas adsorption data of the core sample corresponding to various temperatures in a first-class pressure environment with low pressure through the experimental tests.

S103: establishing a first shale molecular dynamics model for the core sample.

In this embodiment, the first shale molecular dynamics model specifically may be understood as a model structure established based on mineral components of the core sample and capable of reflecting thermodynamic motions of molecules in the system of the core sample.

In one embodiment, during implementation, establishing the first shale molecular dynamics model for the core sample specifically may comprise: performing a total rock diffraction mineral measurement on the core sample to determine contents of various minerals in the core sample; and establishing the first shale molecular dynamics model for the core sample based on the composite structure of clay minerals and organic matters and the contents of the various minerals in the core sample.

In one embodiment, the total rock diffraction mineral measurement may be carried out on the core sample using a benchtop X-ray diffraction analyzer with brand OLYMPUS and type BTX, casting thin-section, and a polarizing microscope with brand LEICA and type DMLP according to oil and gas industry standards 'Quantitative Analysis Method of Rock Mineral Energy Spectrum' (SY/T 6189-2018) and 'Identification of Heavy Minerals in Core' (Q/SYDQ 0343-2000), so as to determine species of minerals in the core sample and contents of the minerals, thereby determining mineral components of the core sample.

In one embodiment, the first shale molecular dynamics model for the core sample may be established in a perspective of composition of clay minerals and organic matters using software Materials Studio (hereinafter referred to as MS) based on the mineral components of the core sample obtained as above.

S104: adjusting the first shale molecular dynamics model based on the shale gas adsorption data of the core sample corresponding to the various temperatures in the first-class pressure environment to obtain a second shale molecular dynamics model.

In one embodiment, adjusting the first shale molecular dynamics model based on the shale gas adsorption data of the core sample corresponding to the various temperatures in the first-class pressure environment to obtain the second shale molecular dynamics model specifically may comprise:

S1: establishing an adsorption characteristic curve of the core sample in a first-class pressure range, based on the shale gas adsorption data of the core sample corresponding to the various temperatures in the first-class pressure environment;

S2: adjusting the mineral contents and model parameters involved in the first shale molecular dynamics model by fitting the adsorption characteristic curve of the core sample in the first-class pressure range, to obtain the second shale molecular dynamics model.

In one embodiment, the obtained first shale molecular dynamics model may be used to perform isothermal adsorption test simulations at various temperatures in the first-class pressure environment, and then a comparison fitting is performed on the first shale molecular dynamics model based on the adsorption characteristic curve of the core sample in the first-class pressure range previously obtained through the experimental tests. During the comparison fitting, data such as the mineral contents and model parameters involved in the first shale molecular dynamics model are modified and adjusted pertinently, so as to obtain a modified and adjusted theoretical model capable of accurately reflecting the actual deep shale characteristics of the target area, wherein the theoretical model is taken as the second shale molecular dynamics model.

According to the above embodiments, the highly accurate shale gas adsorption data of the core sample corresponding to the various temperatures in the first-class pressure environment, which is previously obtained through the experimental tests, can be fully utilized to modify and adjust the first shale molecular dynamics model pertinently, so as to obtain the second shale molecular dynamics model with higher accuracy and better effect and matching the shale characteristics of the target area.

S105: obtaining shale gas adsorption data of the core sample corresponding to the various temperatures in a second-class pressure environment by analog simulation using the second shale molecular dynamics model.

In one embodiment, obtaining the shale gas adsorption data of the core sample corresponding to the various temperatures in the second-class pressure environment by analog simulation using the second shale molecular dynamics model may comprise:

S1: configuring a plurality of matched pressure environment variables based on the second-class pressure environment, wherein the second-class pressure environment comprises a plurality of pressures with pressure values greater than a preset pressure threshold;

S2: performing, by the second shale molecular dynamics model, isothermal adsorption molecular simulations at the various temperatures respectively based on the pressure environment variables, to calculate the shale gas adsorption data of the core sample corresponding to the various temperatures in the second-class pressure environment (i.e., the contents of adsorbed gas in shale corresponding to the various temperatures in the second-class pressure environment).

In one embodiment, the second-class pressure environment specifically may comprise a plurality of pressures with pressure values greater than the preset pressure threshold. The second-class pressure environment may be understood as a pressure set composed of a plurality of pressures with pressure values greater than the preset pressure threshold.

In one embodiment, a higher pressure (i.e., the second-class pressure environment) may be achieved using the second shale molecular dynamics model, and adsorption data corresponding to the higher pressure may be calculated. Specifically, the pressure environment variables of an NPT system in the software MS at a given temperature may be set based on the second-class pressure environment, and an isothermal adsorption molecular simulation may be performed by the second shale molecular dynamics model through the software MS to calculate a corresponding adsorbed gas capacity. In this way, isothermal adsorption molecular simulations are performed at other temperatures respectively, so as to obtain shale gas adsorption data of the core sample corresponding to various temperatures in the second-class pressure environment.

According to the above embodiments, the data obtained by the experimental tests can be combined with the molecular dynamics model, so as to obtain the shale gas adsorption data of the core sample corresponding to the various temperatures in the second-class pressure environment with high pressure, said shale gas adsorption data being accurate and difficult to obtain by the experimental tests.

S106: determining an adsorption characteristic curve of the core sample in a full pressure range, based on the shale gas adsorption data of the core sample corresponding to the various temperatures in the first-class and second-class pressure environments.

In this embodiment, during implementation, the whole and complete shale gas adsorption data can be obtained by comprehensively utilizing the shale gas adsorption data of the core sample corresponding to the various temperatures in the first-class and second-class pressure environments. Furthermore, an adsorption characteristic curve of the core sample in a full pressure range (including the first-class and second-class pressure environments) may be constructed based on the above shale gas adsorption data, the adsorption characteristic curve being more accurate and comprehensive with better use effect. Based on the adsorption characteristic curve, the content of adsorbed gas in a shale corresponding to any combination of pressure (including the pressures in the first-class and second-class pressure environments) and temperature can be determined.

In one embodiment, after the adsorption characteristic curve of the core sample in the full pressure range is determined, during implementation, the method may further comprise: performing a shale gas development in the target area based on the adsorption characteristic curve of the core sample in the full pressure range.

In this embodiment, during implementation, the adsorption characteristic curve in the full pressure range may also be taken as reference data to conduct a shale gas exploration and other operations in the target area.

In one embodiment, during implementation, the method may further comprise: determining adsorption characteristic curves of a plurality of groups of core samples in the full pressure range respectively in the above way, wherein mineral components of core samples in different groups among the plurality of groups of core samples are different from each other; and performing a fitting regression using a multi-factor formula based on the adsorption characteristic curves of the plurality of groups of core samples in the full pressure range, to obtain a deep shale gas adsorption capacity multi-factor prediction model. The deep shale gas adsorption capacity multi-factor prediction model is capable of predicting shale gas adsorption data of the core samples with different mineral components corresponding to different temperatures in different pressure environments.

Thus, when the shale gas development or exploration is carried out in any other area, it is only necessary to obtain core samples in the area and determine mineral components of the core samples in the area. Next, the mineral components are taken as model inputs and inputted into the deep shale gas adsorption capacity multi-factor prediction model. Further, the highly accurate shale gas adsorption data in the full pressure range can be efficiently and conveniently obtained just by running the prediction model, thereby effectively improving processing efficiency of determination of the shale gas adsorption data.

Therefore, when deep shale gas adsorption data is to be determined according to the method provided by the embodiment of the present disclosure, experimental tests are combined with molecular dynamics models. On one hand, firstly, experimental tests are performed on a core sample in a target area at various temperatures in a first-class pressure environment with low pressure, so as to obtain shale gas adsorption data of the core sample corresponding to the various temperatures in the first-class pressure environment. On the other hand, a first shale molecular dynamics model for the core sample is established, and a fitting adjustment is performed on the first shale molecular dynamics model using the previously obtained shale gas adsorption data of the core sample corresponding to the various temperatures in the first-class pressure environment, so as to obtain a second shale molecular dynamics model with higher accuracy and better effect. Further, the second shale molecular dynamics model may be used to obtain, by analog simulation, shale gas adsorption data of the core sample corresponding to the various temperatures in a second-class pressure environment where the pressure is high and the experimental tests are difficult to carry out. Therefore, accurate adsorption data in the second-class pressure environment with high pressure can be obtained by combining the experimental tests with the molecular dynamics models. Further, an accurate and comprehensive adsorption characteristic curve in a full pressure range can be obtained by integrating the adsorption data in the first-class and second-class pressure environments. The method solves the technical problem that it is impossible to obtain accurate and comprehensive adsorption characteristics in a full pressure range due to the lack of adsorption data in the second-class pressure environment with high pressure, the adsorption data being difficult to obtain through the conventional method. Further, a shale gas development can be performed more accurately and effectively in the target area based on the adsorption characteristics in the full pressure range. By adopting the above method, adsorption characteristic curves of a plurality of groups of core samples with different mineral components in the full pressure range are determined respectively, and then subjected to multiple analysis regressions using the multi-factor formula to obtain a deep shale gas adsorption capacity multi-factor prediction model capable of accurately predicting the shale gas adsorption data of the core samples with different mineral components corresponding to different temperatures in different pressure environments. Subsequently, the shale gas adsorption data in a certain area in the full pressure range can be determined quickly and accurately using the deep shale gas adsorption capacity multi-factor prediction model, thereby improving the processing efficiency and reducing the processing cost.

An embodiment of the present disclosure further provides a server, comprising a processor and a memory configured to store instructions executable by the processor. During implementation, the processor may implement the following steps according to the instructions: obtaining a core sample of a target area; performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold; establishing a first shale molecular dynamics model for the core sample; adjusting the first shale molecular dynamics model based on the shale gas adsorption data of the core sample corresponding to the various temperatures in the first-class pressure environment to obtain a second shale molecular dynamics model; obtaining, by analog simulation using the second shale molecular dynamics model, shale gas adsorption data of the core sample corresponding to the various temperatures in a second-class pressure environment; and determining an adsorption characteristic curve of the core sample in a full pressure range based on the shale gas adsorption data of the core sample corresponding to the various temperatures in the first-class and second-class pressure environments.

Figure 2:
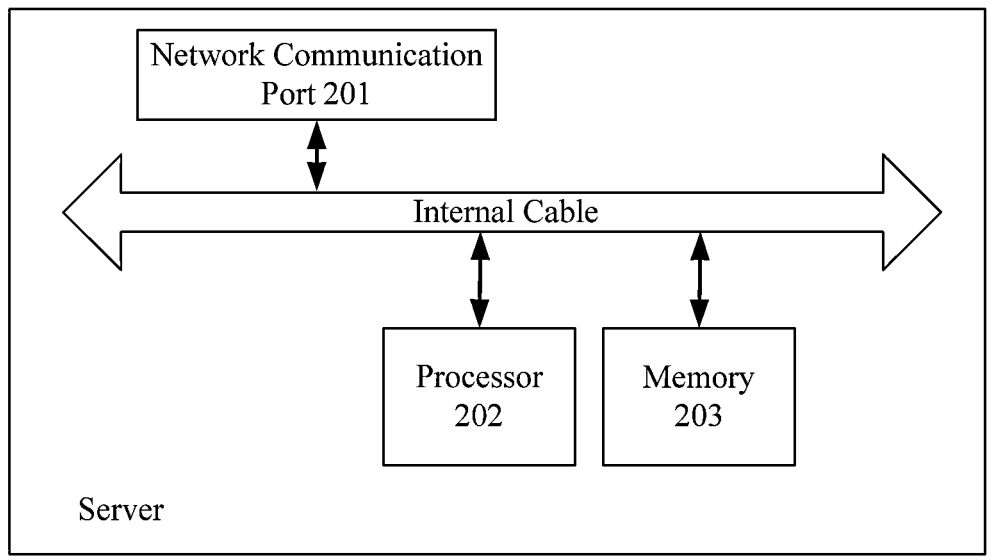
FIG. 2 is a schematic structure diagram of a server provided by an embodiment of the present disclosure.

In order to complete the instructions more accurately, referring to FIG. 2, an embodiment of the present disclosure further provides another specific server, wherein the server comprises a network communication port 201, a processor 202 and a memory 203, which are connected by internal cables, so as to perform specific data interactions.

Specifically, the network communication port 201 may be configured to obtain a core sample of a target area.

Specifically, the processor 202 may be configured to perform tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold; establish a first shale molecular dynamics model for the core sample; adjust the first shale molecular dynamics model based on the shale gas adsorption data of the core sample corresponding to the various temperatures in the first-class pressure environment to obtain a second shale molecular dynamics model; obtain, by analog simulation using the second shale molecular dynamics model, shale gas adsorption data of the core sample corresponding to the various temperatures in a second-class pressure environment; and determine an adsorption characteristic curve of the core sample in a full pressure range based on the shale gas adsorption data of the core sample corresponding to the various temperatures in the first-class and second-class pressure environments.

Specifically, the memory 203 may be configured to store corresponding program instructions.

In this embodiment, the network communication port 201 may be a virtual port bound with different communication protocols to transmit or receive different data. For example, the network communication port may be responsible for web data communications, FTP data communications, or mail data communications. In addition, the network communication port may also be a communication interface of an entity or a communication chip. For example, the network communication port may be a wireless mobile network communication chip, such as GSM, CDMA, etc., or a WiFi chip, or a Bluetooth chip.

In this embodiment, the processor 202 may be implemented in any suitable way. For example, the processor may take the form of, for example, a microprocessor, a processor, a computer-readable medium storing computer-readable program codes (e.g., software or firmware) executable by the (micro) processor, a logic gate, a switch, an Application Specific Integrated Circuit (ASIC), a programmable logic controller, or an embedded microcontroller, etc., which is not limited herein.

In this embodiment, the memory 203 may have a plurality of hierarchies. In a digital system, anyone capable of storing binary data may be used as the memory. In an integrated circuit, a circuit with storage function without a physical form may be also used as the memory, such as a RAM, a FIFO, etc. In a system, a storage device with a physical form may be also used as the memory, such as a memory stick, a TF card, etc.

An embodiment of the present disclosure further provides a computer storage medium based on the method for determining content of adsorbed gas in the deep shale, wherein the computer storage medium stores computer program instructions. When being executed, the computer program instructions implement the following steps: obtaining a core sample of a target area; performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold; establishing a first shale molecular dynamics model for the core sample; adjusting the first shale molecular dynamics model based on the shale gas adsorption data of the core sample corresponding to the various temperatures in the first-class pressure environment to obtain a second shale molecular dynamics model; obtaining, by analog simulation using the second shale molecular dynamics model, shale gas adsorption data of the core sample corresponding to the various temperatures in a second-class pressure environment; and determining an adsorption characteristic curve of the core sample in a full pressure range based on the shale gas adsorption data of the core sample corresponding to the various temperatures in the first-class and second-class pressure environments.

In this embodiment, the storage medium includes but is not limited to a Random-Access Memory (RAM), a Read-Only Memory (ROM), a cache, a Hard Disk Drive (HDD) or a memory card. The memory may be configured to store computer program instructions. A network communication unit may be an interface for network connection communications and provided according to a standard specified by a communication protocol.

In this embodiment, the specific functions and effects of the program instructions stored in the computer storage medium may be explained with reference to other embodiments, and the repetitive description is omitted herein.

Figure 3:
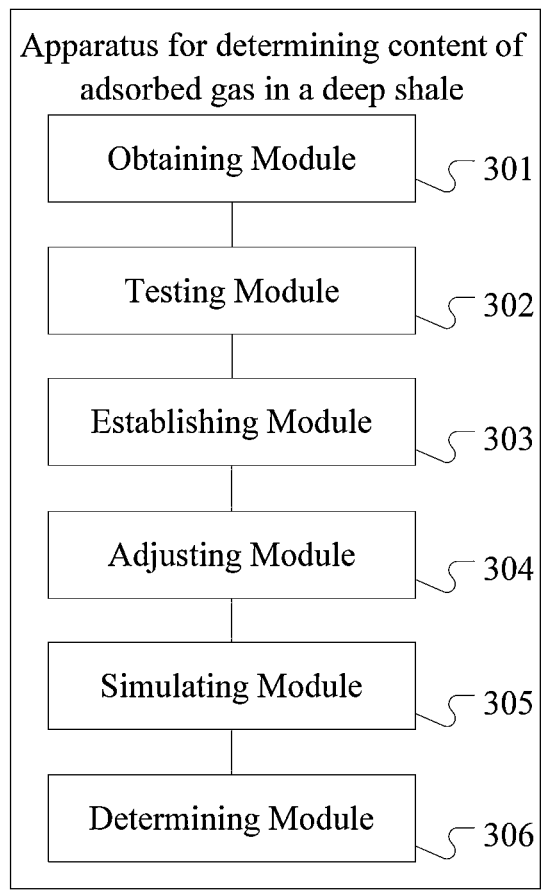
FIG. 3 is a schematic structure diagram of an apparatus for determining content of adsorbed gas in a deep shale provided by an embodiment of the present disclosure.

Referring to FIG. 3, at the software level, an embodiment of the present disclosure further provides an apparatus for determining content of adsorbed gas in a deep shale, which specifically comprises the following structural modules:

an obtaining module 301 configured to obtain a core sample of a target area;

a testing module 302 configured to perform tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold;

an establishing module 303 configured to establish a first shale molecular dynamics model for the core sample;

an adjusting module 304 configured to adjust the first shale molecular dynamics model based on the shale gas adsorption data of the core sample corresponding to the various temperatures in the first-class pressure environment to obtain a second shale molecular dynamics model;

a simulating module 305 configured to obtain, by analog simulation using the second shale molecular dynamics model, shale gas adsorption data of the core sample corresponding to the various temperatures in a second-class pressure environment; and a determining module 306 configured to determine an adsorption characteristic curve of the core sample in a full pressure range based on the shale gas adsorption data of the core sample corresponding to the various temperatures in the first-class and second-class pressure environments.

In one embodiment, the testing module 302 specifically may be configured to perform isothermal adsorption tests on the core sample at the various temperatures in the first-class pressure environment to obtain excess adsorption capacities of shale gas corresponding to the various temperatures; and determine, based on a density of absorbed phase of shale gas and the excess adsorption capacities of shale gas corresponding to the various temperatures, absolute adsorption capacities of shale gas corresponding to the various temperatures as shale gas adsorption data of the core sample corresponding to the various temperatures in the first-class pressure environment.

In one embodiment, the establishing module 303 specifically may be configured to perform a total rock diffraction mineral measurement on the core sample to determine contents of various minerals in the core sample; and establish the first shale molecular dynamics model for the core sample in a dimension of composition of clay minerals and organic matters based on the contents of the various minerals in the core sample.

In one embodiment, the adjusting module 304 specifically may be configured to establish an adsorption characteristic curve of the core sample in a first-class pressure range, based on the shale gas adsorption data of the core sample corresponding to the various temperatures in the first-class pressure environment; and adjust mineral contents and model parameters involved in the first shale molecular dynamics model by fitting the adsorption characteristic curve of the core sample in the first-class pressure range, to obtain the second shale molecular dynamics model.

In one embodiment, the simulating module 305 specifically may be configured to configure a plurality of matched pressure environment variables based on the second-class pressure environment, wherein the second-class pressure environment comprises a plurality of pressures with pressure values greater than a preset pressure threshold; and perform, by the second shale molecular dynamics model, isothermal adsorption molecular simulations at the various temperatures respectively based on the matched pressure environment variables, to calculate the shale gas adsorption data of the core sample corresponding to the various temperatures in the second-class pressure environment.

In one embodiment, the apparatus may further comprise an application module that specifically may be configured to perform a shale gas development in the target area according to the adsorption characteristic curve of the core sample in the full pressure range.

It should be noted that any unit, device or module set forth in the above embodiments specifically may be implemented by a computer chip or an entity, or by a product having a certain function. For the sake of description, when the above apparatus is described, the functions are divided into various modules and described separately. Apparently, the functions of the modules can be implemented in one or more software and/or hardware components. A module realizing a function may also be implemented by a combination of multiple sub-modules or sub-units. The implementations of the apparatus described above are merely illustrative. For example, a division of units are just for a logical division of functions. Another way of division can exist in an actual implementation. For example, a plurality of units or components may be combined or may be integrated into another system, or some features may be omitted or not executed. In addition, the mutual coupling or direct coupling or communication connection illustrated or discussed may be an indirect coupling or communication connection through some interfaces, means or units, and may be in electrical, mechanical or other forms.

It is clear that according to the apparatus for determining content of adsorbed gas in a deep shale provided by the embodiment of the present disclosure, accurate adsorption data in a second-class pressure environment with high pressure can be obtained by combining experimental tests with molecular dynamics models, and an accurate and comprehensive adsorption characteristic curve in a full pressure range can be obtained by integrating the adsorption data in the first-class and second-class pressure environments.

Figure 4:
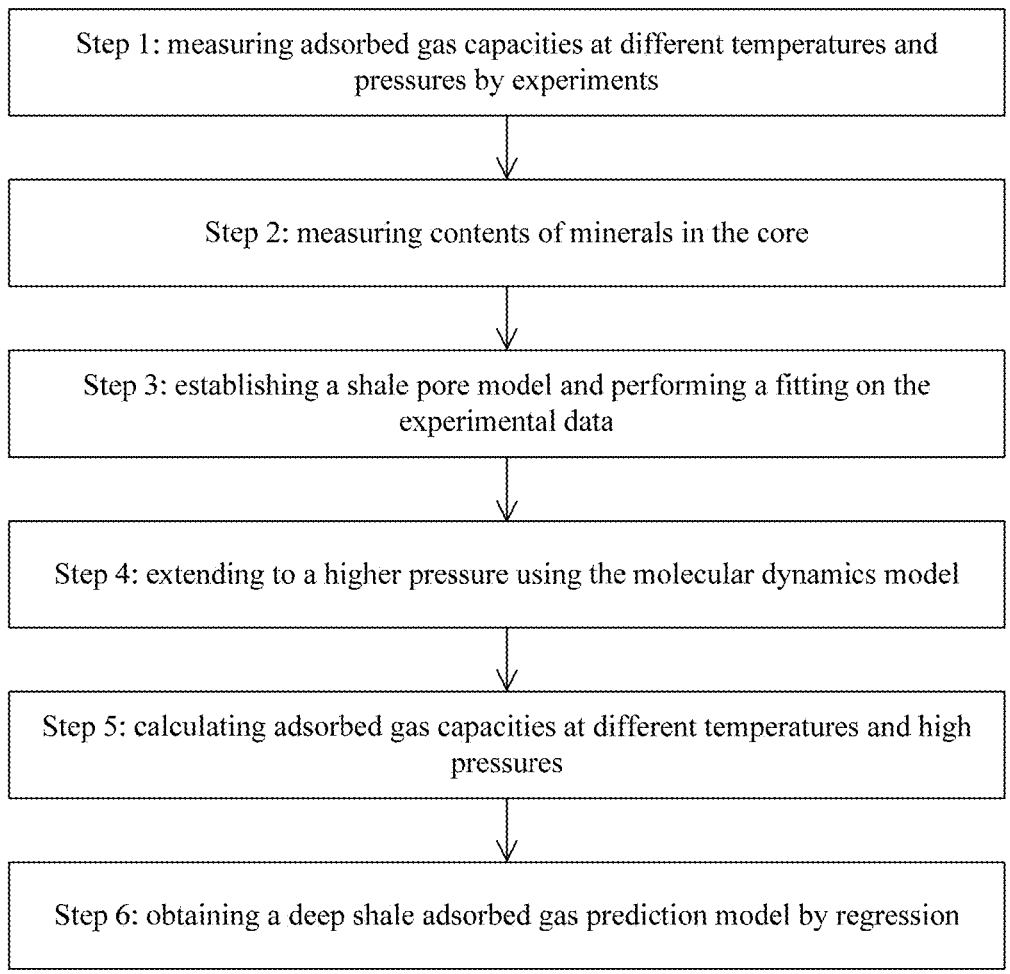
FIG. 4 is a schematic diagram of an implementation in which a method for determining content of adsorbed gas in a deep shale provided by an embodiment of the present disclosure is applied in a scenario example.

In a specific scenario example, the method for determining content of adsorbed gas in the deep shale provided by the present disclosure may be applied to determine deep shale gas adsorption data of a well named XX. Referring to FIG. 4, the specific implementation process comprises the following steps.

(1) Measuring adsorbed gas capacities at a temperature under different pressure conditions (e.g., shale gas adsorption data of the core sample corresponding to a temperature in a first-class pressure environment) using an experimental test method.

The experimental test may be specifically performed using a self-developed shale gas isothermal adsorption experimental apparatus according to experimental rules specified in national standard GB/T19560-2004 'Experimental Method of High-Pressure Adsorption Isothermal to Coal-Capacity Method' of China. In the shale gas isothermal adsorption experimental apparatus, a reference kettle and a sample kettle are both made of stainless steel, and each equipped with a pressure sensor to measure gas pressure therein. A maximum bearable pressure of the pressure sensor may be 35 MPa with an accuracy of 0.03%.

The shale adsorption is a single-component adsorption of methane, with an experimental temperature of 40-80° C. and a pressure of 0-20 MPa. The experimental steps are as follows.

S1: preforming a preprocess on a core sample;

S2: checking tightness of the apparatus;

S3: calibrating volumes of a reference kettle and a sample kettle;

S4: calibrating volumes of a middle area and a free area;

S5: performing a shale gas single-component isothermal adsorption experiment.

Specifically, setting a temperature and evacuating the whole experimental system, and then injecting high-pressure gas into the reference kettle until the pressure is stable. Next, the gas in the reference kettle is gradually transferred to the sample kettle by opening and closing corresponding pneumatic valves. It should be noted that the reference kettle and the sample kettle remain disconnected to each other during the whole experiment. Finally, an excess adsorption capacity of methane is obtained based on the law of conservation of mass.

S6: replacing the core sample with another core sample and repeating step S5, until all of the core samples are tested.

S7: converting the excess adsorption capacities obtained in the experiment into absolute adsorption capacities.

Specifically, the density of adsorbed phase of shale gas under a high pressure may firstly be studied in an optimized method, without making any assumption on the state of the adsorbed phase. Further, the density of adsorbed phase may be taken as an unknown number to participate in fitting, and then the fitting result is compared with a density of adsorbed phase calculated in the prior art.

According to a Gibbs excess adsorption isotherm, the relationship between the excess adsorption capacity and the absolute adsorption capacity is:

$$n_{exc}^{Gibbs} = n_{ads}^{Abs}\left(1 - \frac{\rho_{gas}}{\rho_{ads}}\right) \quad (1)$$

According to a Langmuir equation, the basic form is:

$$n_{abs} = n_L \frac{bP}{1 + bP} \quad (2)$$

Thus, the corrected relationship between the excess adsorption capacity and the absolute adsorption capacity is:

$$n_{exc} = n_L \frac{bP}{1 + bP}\left(1 - \frac{\rho_{gas}}{\rho_{ads}}\right) \quad (3)$$

The density of adsorbed phase may be treated as an atmospheric boiling point density, i.e., $\rho_{ads}=0.421$ g/cm$^3$ may be substituted into equation (3) to obtain an absolute adsorption capacity by fitting.

(2) Changing the experimental temperature and measuring the adsorbed gas capacities corresponding to the temperature under different pressure conditions (e.g., shale gas adsorption data of the core sample corresponding to various temperatures in the first-class pressure environment);

Changing the set temperature, and repeating steps S5, S6 and S7 in step (1) to perform adsorption experiments to obtain adsorbed gas capacities at different temperatures and pressures.

(3) Determining contents of various minerals (e.g., mineral components) in the shale core used in the adsorption experiment.

Specifically, the total rock diffraction mineral measurement may be carried out on the core sample using a benchtop X-ray diffraction analyzer with brand OLYMPUS and type BTX, casting sheets and a polarizing microscope with brand LEICA and type DMLP according to oil and gas industry standards 'Quantitative Analysis Method of Rock Mineral Energy Spectrum' (SY/T 6189-2018) and 'Identification of Heavy Minerals in Core' (Q/SYDQ 0343-2000).

(4) Establishing a shale pore model based on the mineral components, and performing a fitting on the shale gas adsorption-desorption curve at different temperatures measured by experiments (e.g., the adsorption characteristic curve of the core sample in the first pressure range) by adjusting the mineral contents.

Specifically, based on the mineral analysis result, the present disclosure uses software Materials Studio (hereinafter referred to as MS) to establish a composite model (e.g., a first shale molecular dynamics model) based on the composite structure of clay minerals and organic matters, carries out adsorption quantity simulations at pressures and temperatures within the experimental range, and obtains a final representative theoretical model (e.g., a second shale molecular dynamics model) that best reflects the actual deep shale characteristics after selecting and comparing various parameters.

(5) Using the fitted shale molecular dynamics model to reach a higher pressure and calculate an adsorbed gas capacity (e.g., the shale gas adsorption data of the core sample corresponding to a certain temperature in the second-class pressure environment).

Based on the final representative theoretical model, pressure environment variables of an NPT system in the software MS are increased at a given temperature, and isothermal adsorption molecular simulation is carried out to calculate a corresponding adsorbed gas capacity.

(6) Calculating adsorption capacities of shale gas at different temperatures and high pressures respectively (i.e., the shale gas adsorption data of the core sample corresponding to the various temperatures in the second-class pressure environment).

Similarly, temperature variables are further adjusted, and a methane adsorption molecular simulation is carried out at high temperatures and high pressures to calculate corresponding adsorbed gas capacities.

(7) obtaining a deep shale gas adsorption capacity multi-factor prediction model by regression.

Specifically, the multi-factor formula may be adopted to perform a multiple analysis regression, so as to obtain a deep shale gas adsorption capacity multi-factor prediction model and a full-range adsorption characteristic curve (e.g., an adsorption characteristic curve of the core sample in a full pressure range).

Figure 5:
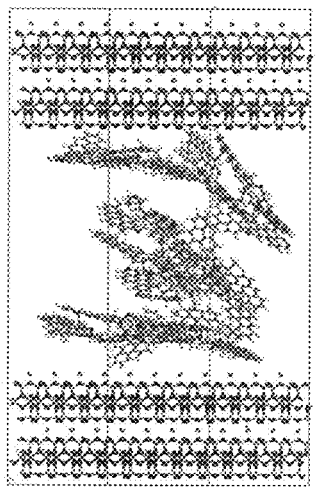
FIG. 5 is a schematic diagram of an implementation in which a method for determining content of adsorbed gas in a deep shale provided by an embodiment of the present disclosure is applied in a scenario example.
Figure 6A:
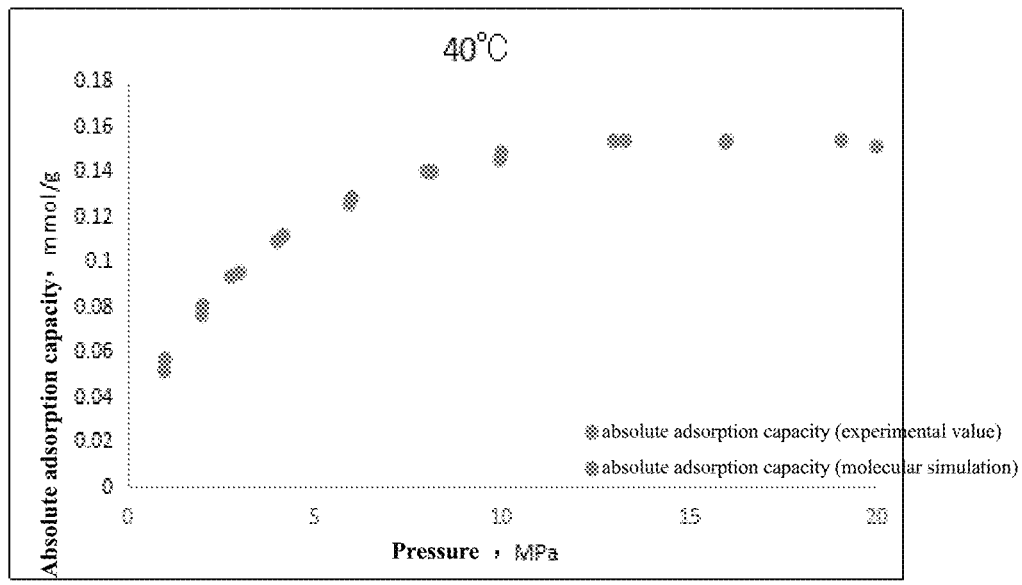
FIGS. 6(a)-6(e) are schematic diagrams of implementations in which a method for determining content of adsorbed gas in a deep shale provided by an embodiment of the present disclosure is applied in a scenario example.
Figure 6B:
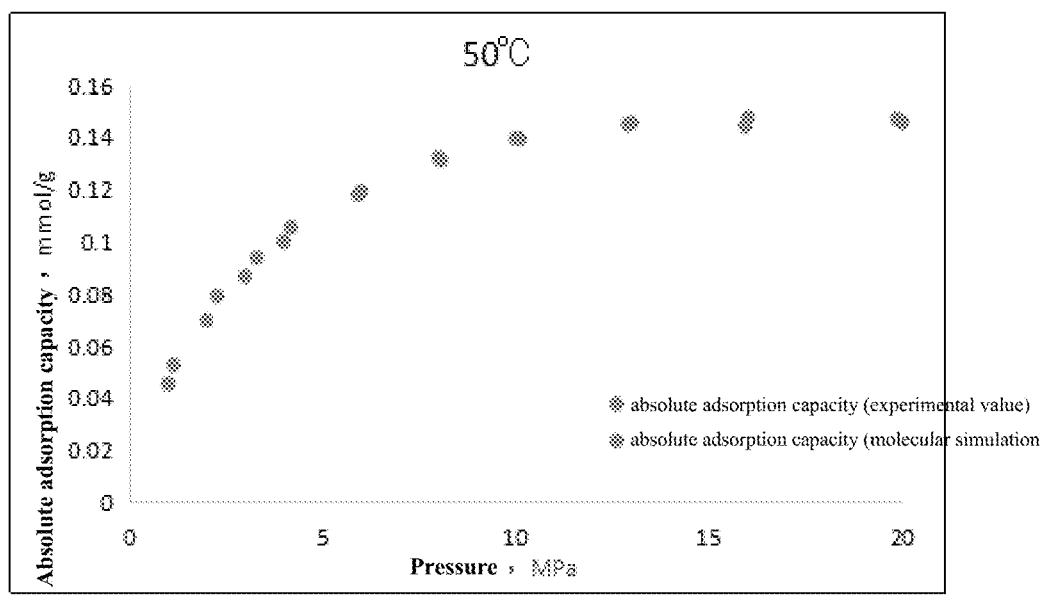
Figure 6C:
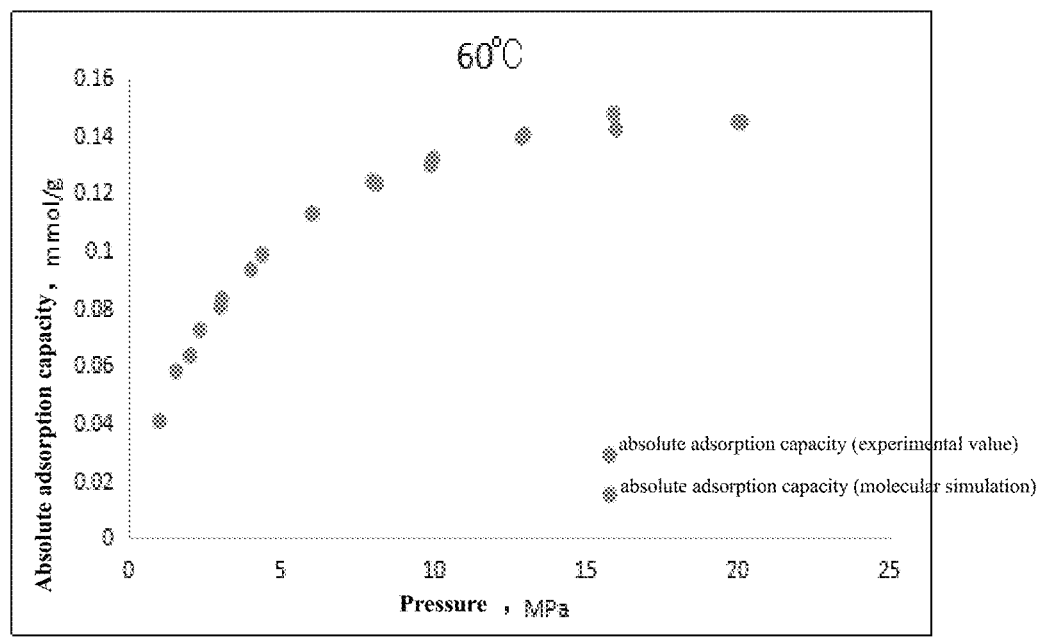
Figure 6D:
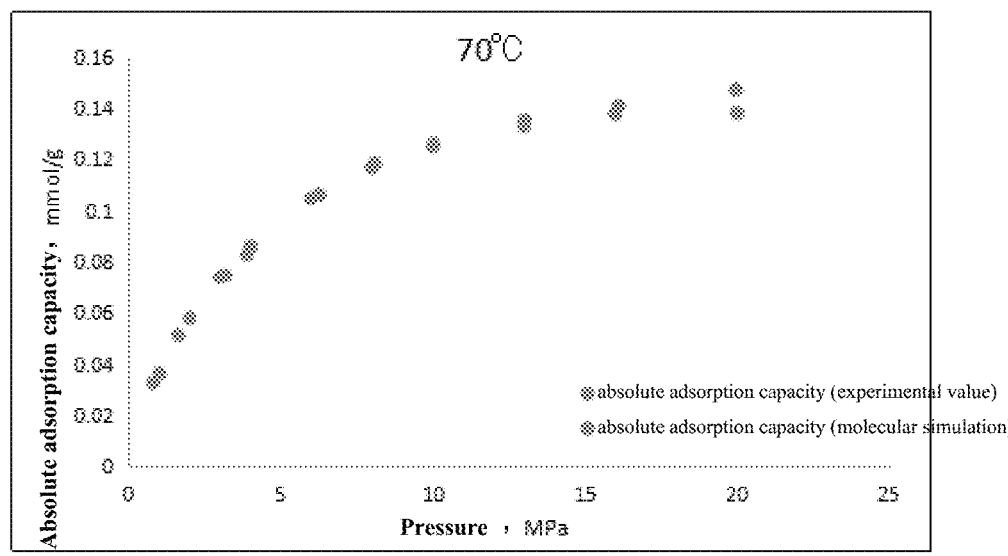
Figure 6E:
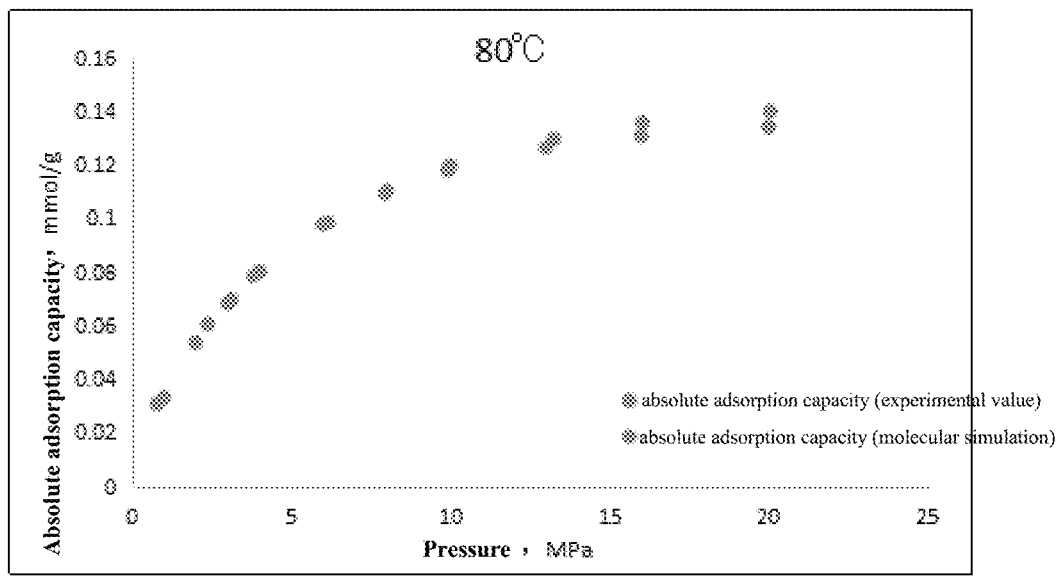

Specifically, taking a well named XX as an example, a final model structure—an illite plus kerogen composite model (see FIG. 5), i.e., a second shale molecular dynamics model, is screened out by adjustment based on a fitting result of simulation data and experimental data, wherein kerogen accounts for 15.1%. The existing experimental results are adopted to fit and verify the model (see FIG. 6). It can be seen from the model that the fitting results are satisfactory at all temperature points and within the full pressure range, so it is considered that the model can represent a pore model of an actual stratum. FIG. 6 illustrates fitting of experimental and molecular simulation results, wherein the letter a corresponds to 40° C., the letter b corresponds to 50° C., the letter c corresponds to 60° C., the letter c corresponds to 70° C., and the letter e corresponds to 80° C.

Figure 7:
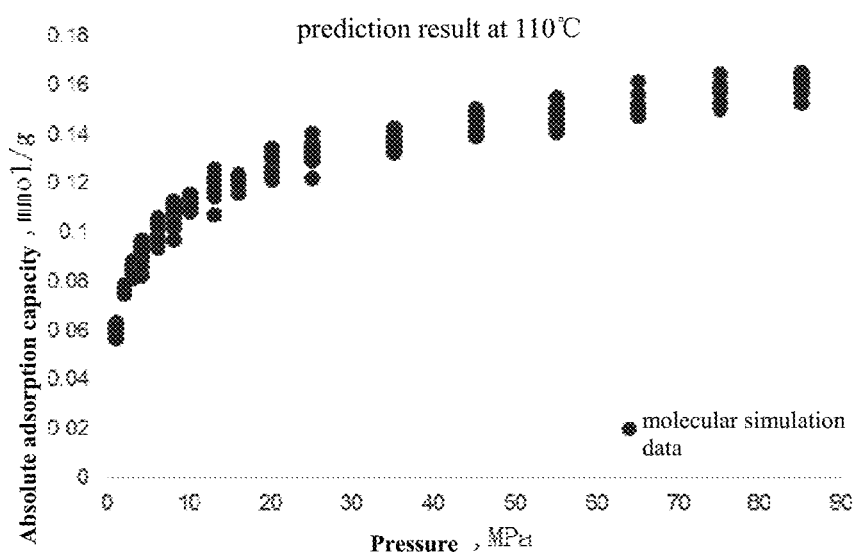
FIG. 7 is a schematic diagram of an implementation in which a method for determining content of adsorbed gas in a deep shale provided by an embodiment of the present disclosure is applied in a scenario example.

Further, the model may be used to simulate the adsorption characteristics at a reservoir temperature of 110° C. (see FIG. 7). According to a mean difference variation at each pressure point, it can be judged that at 75-85 MPa the adsorption capacity is close to a stable value and is about 0.156 mmol/g.

Figure 8:
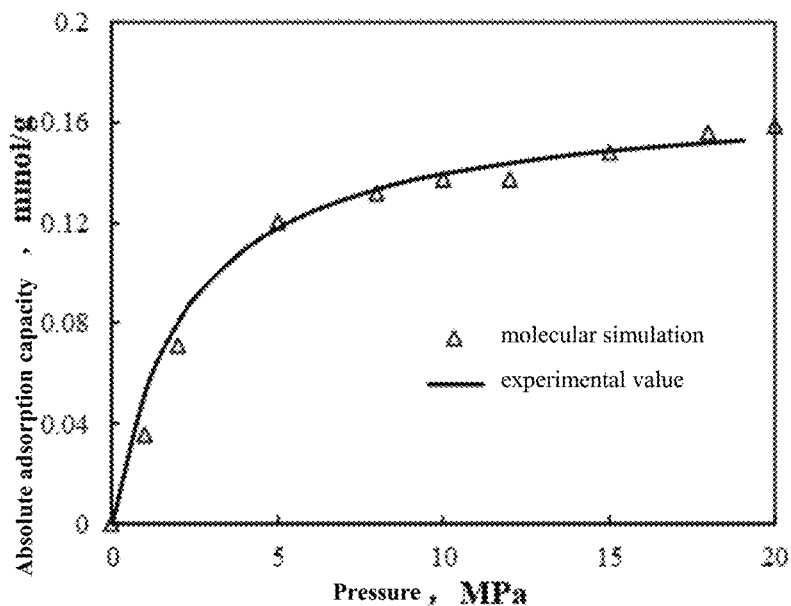
FIG. 8 is a schematic diagram of an implementation in which a method for determining content of adsorbed gas in a deep shale provided by an embodiment of the present disclosure is applied in a scenario example.
Figure 9:
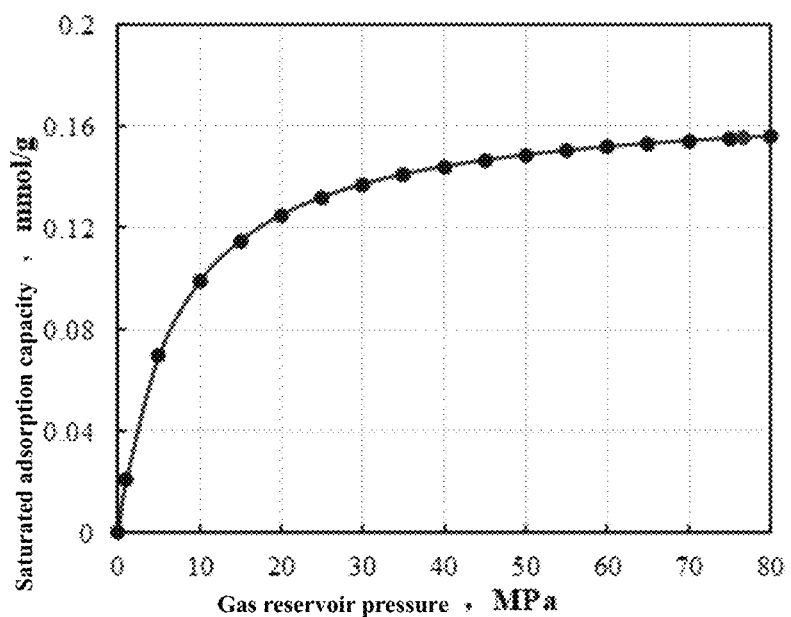
FIG. 9 is a schematic diagram of an implementation in which a method for determining content of adsorbed gas in a deep shale provided by an embodiment of the present disclosure is applied in a scenario example.
Figure 10:
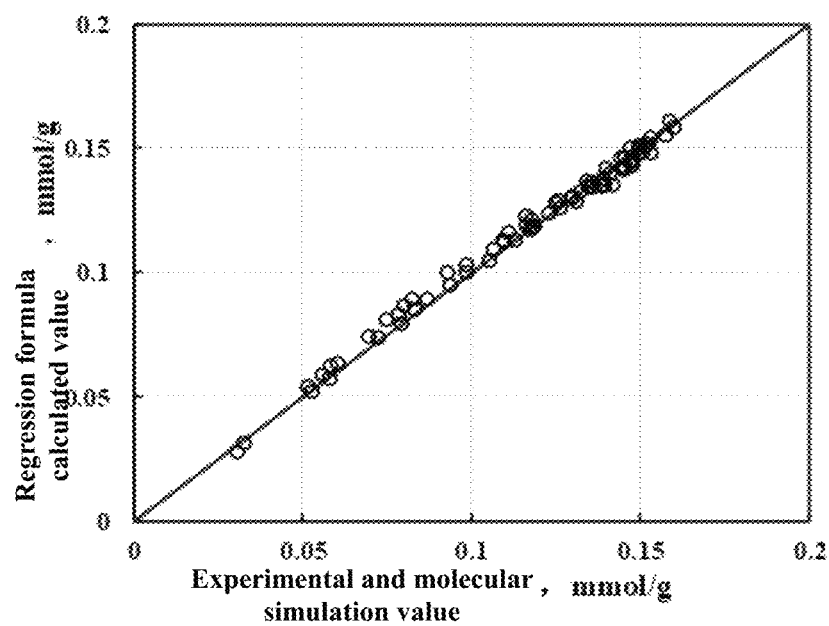
FIG. 10 is a schematic diagram of an implementation in which a method for determining content of adsorbed gas in a deep shale provided by an embodiment of the present disclosure is applied in a scenario example.

Next, the molecular simulations of the absolute adsorption capacities and the experimental values at different pressures may be fitted, as illustrated in FIG. 8. Next, the adsorption capacities at high temperatures and high pressures are predicted by the molecular simulations, and multiple analysis regression is carried out using a multi-factor formula, so as to obtain a deep shale gas adsorption capacity multi-factor prediction model and a full-rage adsorption characteristic curve (see FIG. 9). The model prediction result and the experiment and molecular simulation comparison result are illustrated in FIG. 10. The deep shale gas adsorption capacity multi-factor prediction model may be represented as $$n_{abs} = (-0.004 + 0.01 \cdot TOC + 0.007 \cdot R_o + 0.007 \cdot BET + 0.0026 \cdot IS) \times \frac{\exp(1600/T - 6.3) \cdot P}{1 + \exp(1600/T - 6.3) \cdot P},$$

wherein TOC denotes a total organic carbon content, $R_o$ denotes a maturity, BET denotes a specific surface area, IS denotes content of an illite/smectite mixed layer, T denotes a temperature.

Through the above scenario examples, it verifies the means adopted by the method for determining the deep shale adsorbed gas content provided by the present disclosure, i.e., comprehensively utilizing indoor physical simulation experiments (e.g., experimental tests) and molecular dynamics simulations for joint measurement, realizes adsorption characteristics tests of the deep shale adsorption at all temperatures and within a full pressure range, and accurately determines the adsorption data in the full pressure range, thereby better guiding the evaluation and efficient development of the shale gas resources.

Although the present disclosure provides the method operations as described in the implementations or flowcharts, more or fewer operations may be included based on the conventional or non-inventive efforts. The order of operations listed in the implementations is only one of the many orders of execution and does not meant to be the only order of execution. When an actual device or terminal product is executed, execution can be performed sequentially or in parallel according to the order described in the method of the implementation or the drawings (e.g., in parallel processor or multi-threaded environment, even for distributed data processing environments). The term 'comprising', 'including' or any other variant is intended to cover the non-exclusive inclusions, so that a series of elements including the process, method, product or device comprise not only those elements, but also comprise other elements not explicitly listed, or inherent elements included in the process, method, product or device. In the absence of more restrictions, the process, method, article, or apparatus include the elements does not exclude an existence of additional identical or equivalent elements. The terms 'first', 'second', etc. indicate names, rather than any particular order.

One skilled in the art also knows that there are other methods implementing a controller in addition to pure computer readable program codes. Logic programming of the methods may be performed to implement the same functionalities using a way such as controlling logic gates, switches, application specific integrated circuits, programmable logic controllers, and embedded microcontrollers. Therefore, this controller may be considered to be a hardware component, and include modules for implementing various functions and being considered as a part of hardware structures. Alternatively, those apparatuses for implementing various functions may even be considered as not only software modules for implementing a method, but also the hardware structures The present application may be described in the general context of computer-executable instructions executed by a computer, such as program modules. In general, program modules include routines, programs, objects, components, data structures, etc., that perform specific tasks or implement specific abstract data types. The embodiments of the present disclosure may also be implemented in a distributed computing environment. In these distributed computing environments, tasks are performed by a remote processing device connected via a communication network. In a distributed computing environment, the program modules may be located in local and remote computer storage media, including storage devices.

As can be seen from the description of the above embodiments, those skilled in the art can clearly understand that the present disclosure can be implemented by means of software plus a necessary universal hardware platform. Based on this understanding, the essence of the technical solution of the present disclosure can be embodied in the form of a computer software product, which may be stored in a storage medium, such as a ROM/RAM, a magnetic disk, an optical disk, etc., and include several instructions to enable a computer apparatus (a personal computer, a server, a network apparatus, etc.) to carry out the embodiments of the present disclosure, or the methods described in some parts of the embodiments.

The various embodiments in the disclosure are described in a progressive manner, and the same or similar parts between the various embodiments may be referred to each other, and each embodiment focuses on the differences from the other embodiments. The present disclosure is applicable to a lot of general or dedicated computer system environments or configurations, such as a personal computer, a server computer, a handheld or portable apparatus, a tablet apparatus, a multiprocessor system, a microprocessor-based system, a set-top box, a programmable consumer electronic apparatus, a network PC, a minicomputer, a mainframe computer, a distributed computing environment including any of the above systems or apparatus, etc.

Although the present disclosure has been described through the embodiments, those of ordinary skills in the art know that there are many modifications and variations to the present disclosure without departing from the spirit of the present disclosure, and it is intended that the appended claims include those modifications and variations without departing from the spirit of the present disclosure.

The invention claimed is:

1. A method for determining content of adsorbed gas in a deep shale, comprising:
    obtaining a core sample of a target area;
    performing tests on the core sample at various temperatures in a first-class pressure environment to obtain shale gas adsorption data of the core sample corresponding to the various temperatures in the first-class pressure environment, wherein the first-class pressure environment comprises a plurality of pressures with pressure values less than or equal to a preset pressure threshold;

establishing a first shale molecular dynamics model for the core sample;

adjusting the first shale molecular dynamics model based on the shale gas adsorption data of the core sample corresponding to the various temperatures in the first-class pressure environment to obtain a second shale molecular dynamics model;

obtaining, by analog simulation using the second shale molecular dynamics model, shale gas adsorption data of the core sample corresponding to the various temperatures in a second-class pressure environment, comprising:

selecting a plurality of pressure environment variables matched with pressures of the target area from the second-class pressure environment, wherein the second-class pressure environment comprises a plurality of pressures with pressure values greater than a preset pressure threshold; and performing, by the second shale molecular dynamics model, isothermal adsorption molecular simulations at the various temperatures respectively based on the pressure environment variables, to calculate the shale gas adsorption data of the core sample corresponding to the various temperatures in the second-class pressure environment; and determining an adsorption characteristic curve of the core sample in a full pressure range, based on the shale gas adsorption data of the core sample corresponding to the various temperatures in the first-class and second-class pressure environments.

2. The method according to claim 1, wherein performing tests on the core sample at the various temperatures in the first-class pressure environment to obtain shale gas adsorption data of the core sample corresponding to the various temperatures in the first-class pressure environment comprises:

performing isothermal adsorption tests on the core sample at the various temperatures in the first-class pressure environment to obtain excess adsorption capacities of shale gas corresponding to the various temperatures; and calculating, based on the excess adsorption capacities of shale gas corresponding to the various temperatures, absolute adsorption capacities of shale gas corresponding to the various temperatures, as the shale gas adsorption data of the core sample corresponding to the various temperatures in the first-class pressure environment.

3. The method according to claim 1, wherein establishing the first shale molecular dynamics model for the core sample comprises:

performing a total rock diffraction mineral measurement on the core sample to determine contents of various minerals in the core sample; and establishing the first shale molecular dynamics model for the core sample based on composite structure of clay minerals and organic matters and the contents of the various minerals in the core sample.

4. The method according to claim 3, wherein adjusting the first shale molecular dynamics model based on the shale gas adsorption data of the core sample corresponding to the various temperatures in the first-class pressure environment to obtain the second shale molecular dynamics model comprises:

establishing an adsorption characteristic curve of the core sample in a first-class pressure range, based on the shale gas adsorption data of the core sample corresponding to the various temperatures in the first-class pressure environment; and adjusting the contents of the minerals and model parameters involved in the first shale molecular dynamics model by fitting the adsorption characteristic curve of the core sample in the first-class pressure range, to obtain the second shale molecular dynamics model.

5. The method according to claim 1, wherein after determining the adsorption characteristic curve of the core sample in the full pressure range, the method further comprises:

performing a shale gas development in the target area based on the adsorption characteristic curve of the core sample in the full pressure range.

6. The method according to claim 1, further comprising:

determining adsorption characteristic curves of a plurality of groups of core samples in the full pressure range, wherein mineral components of core samples in different groups among the plurality of groups of core samples are different from each other;

performing a fitting regression using a multi-factor formula based on the adsorption characteristic curves of the plurality of groups of core samples in the full pressure range to obtain a deep shale gas adsorption capacity multi-factor prediction model, wherein the deep shale gas adsorption capacity multi-factor prediction model is capable of predicting shale gas adsorption data of the core samples with different mineral components corresponding to different temperatures in different pressure environments.

7. A server, comprising a processor and a memory configured to store instructions executable by the processor, the processor is configured to execute the instructions to implement the following steps of the claim 1:

establishing a first shale molecular dynamics model for the core sample;

adjusting the first shale molecular dynamics model based on the shale gas adsorption data of the core sample corresponding to the various temperatures in the first-class pressure environment to obtain a second shale molecular dynamics model;

obtaining, by analog simulation using the second shale molecular dynamics model, shale gas adsorption data of the core sample corresponding to the various temperatures in a second-class pressure environment, comprising:

selecting a plurality of pressure environment variables matched with pressures of the target area from the second-class pressure environment, wherein the second-class pressure environment comprises a plurality of pressures with pressure values greater than a preset pressure threshold; and performing, by the second shale molecular dynamics model, isothermal adsorption molecular simulations at the various temperatures respectively based on the pressure environment variables, to calculate the shale gas adsorption data of the core sample corresponding to the various temperatures in the second-class pressure environment; and determining an adsorption characteristic curve of the core sample in a full pressure range, based on the shale gas adsorption data of the core sample corresponding to the various temperatures in the first-class and second-class pressure environments.

* * * * *